United States Patent [19]

Montagna et al.

[11] Patent Number: 5,814,698
[45] Date of Patent: Sep. 29, 1998

[54] POLYTETRAFLUOROETHYLENE DISPERSIONS IN AN ORGANIC SOLVENT AND DISPERSING AGENTS EMPLOYED THEREIN

[75] Inventors: Laura Montagna, Arese; Ezio Strepparola, Treviglio, both of Italy

[73] Assignee: Ausimont S.p.A., Milan, Italy

[21] Appl. No.: 620,572

[22] Filed: Mar. 22, 1996

[30] Foreign Application Priority Data

Mar. 24, 1995 [IT] Italy .................. MI95A0593

[51] Int. Cl.⁶ .................. C08J 51/00; C08K 51/00; C08L 27/12
[52] U.S. Cl. .................. 524/544; 528/401; 528/402; 568/560; 568/615; 568/677; 568/683; 427/302
[58] Field of Search .................. 524/544; 528/402, 528/401; 568/560, 615, 677, 683; 424/302

[56] References Cited

U.S. PATENT DOCUMENTS

| | | |
|---|---|---|
| 3,242,218 | 3/1966 | Miller . |
| 3,352,811 | 11/1967 | Stand .................. 260/31.2 |
| 3,631,141 | 12/1971 | Fang . |
| 3,715,378 | 2/1973 | Sianesi et al. . |
| 3,810,874 | 5/1974 | Mitsch et al. . |
| 4,523,039 | 6/1985 | Lagow et al. . |
| 4,647,413 | 3/1987 | Savu . |
| 5,149,842 | 9/1992 | Sianesi et al. . |
| 5,258,110 | 11/1993 | Sianesi et al. . |

FOREIGN PATENT DOCUMENTS

| | | |
|---|---|---|
| 0148482A2 | 7/1985 | European Pat. Off. . |
| 0239123A2 | 9/1987 | European Pat. Off. . |
| 254269 | 1/1988 | European Pat. Off. . |
| 0340740A2 | 11/1989 | European Pat. Off. . |
| 556770 | 8/1993 | European Pat. Off. . |
| 138986 | 12/1979 | Germany . |
| 1104482 | 2/1968 | United Kingdom . |
| 9003357 | 4/1990 | WIPO . |

OTHER PUBLICATIONS

European Search Report issued in European applicaton no. 96104482.3 on Dec. 12, 1996.

*Primary Examiner*—Duc Truong
*Attorney, Agent, or Firm*—Nikaido, Marmelstein, Murray & Oram, LLP

[57] ABSTRACT

Polytetrafluoroethylene (PTFE) dispersions in an organic solvent, comprising:

(A) from 2 to 40% by weight of PTFE in powder form;
(B) from 50 to 95% by weight of an organic solvent;
(C) from 0.5 to 10% by weight of a dispersing agent of formula:

$$(R_H-L)_y-(R_F-L)_xR_H \qquad (I)$$

wherein:
x is an integer from 1 to 3;
y is 0 or 1, with the proviso that x=1 when y=1;
$R_H$ is a x-functional radical having an alkylic or polyoxyalkylenic structure;
$R_F$ is (per)fluoropolyoxyalkylenic radical;
L is a divalent organic group.

Such dispersions are utilized for the surface treatment of metals, glass fibers, and the like, and in particular as mold release agents.

11 Claims, No Drawings

POLYTETRAFLUOROETHYLENE DISPERSIONS IN AN ORGANIC SOLVENT AND DISPERSING AGENTS EMPLOYED THEREIN

The present invention relates to polytetrafluoroethylene dispersions in an organic solvent and to the dispersing agents employed therein.

Polytetrafluoroethylene (PTFE) dispersions in an aqueous medium are known, which can be employed for the surface treatment of various materials, for instance metals, glass fibers and the like, in order to obtain a protective, lubricating and anti-adhesive effect.

A typical employment of such dispersions is as release agent for molding thermoplastic polymers or thermosetting resins (polyvinylchloride, epoxy resins, polyurethanes, polyesters, etc.). The PTFE adhesion to the mould surface results, however, poor wherefore complex and expensive pretreatments are generally necessary, for instance PTFE sintering processes, unfeasible in case of moulds which can strain at high temperatures. Moreover, the presence of water in the dispersions involves removal problems, especially when the treated material requires relatively low working temperatures, and possible interaction with the components of the resin to be moulded (for instance with isocyanates). At last, such dispersions generally show poor stability, wherefore irreversible separation of PTFE coagula occurs, both owing to simple ageing and to external stresses (heating or cooling, mechanical stirring, addition of electrolytes, etc.).

PTFE dispersions in various organic mediums are also known. For instance U.S. Pat. No. 3,631,141 describes PTFE dispersions in organic medium, prepared according to a complex method which requires the employment of a PTFE aqueous dispersion, to which an organic solvent is added capable to form an azeotropic mixture with water (for instance ter.butanol or a ter.butanol/cyclohexane mixture). By continuous distillation of the azeotrope, water is removed till obtaining a substantially anhydrous dispersion. The drawbacks of such a method of preparation are evident, both for its complexity and for the limited choice of solvents capable to form an azeotrope with water.

Other known PTFE dispersions are those wherein the organic medium is formed by a chlorofluorocarbon (CFC), in particular CFC-113 ($CCl_2F$—$CClF_2$). As known, however CFC have a depleting effect on the ozone present in the stratosphere, wherefore their use is forbidden or anyway strongly limited. Such dispesions show moreover poor stability and low degree of adhesion to metals. This fact is a remarkable drawback in particular for the use as release agent from moulds. In fact, PTFE tends to move on the molded piece, by modifying the surface characteristics thereof and making difficult the subsequent processings (for instance gluing and painting). The treatment has moreover low efficiency, since it must be repeated after a limited number of moldings.

It has therefore been proposed to replace CFC with other solvents, for instance alcohols, and in particular isopropanol, which show however high inflammability and give dispersions much less stable than in CFC.

In the ex Est Germany patent DD-138,986 it is described the preparation of dispersions by mixing PTFE in powder in an organic solvent, for instance cyclohexane, toluene or methylisobutylketone, in the presence of an hydrocarbon surfactant, for instance an oligomer of ethylenoxide with an alkylphenol or a long chain alcohol. The PTFE dispersion results however rather unstable, wherefore it it necessary to filter the undispersed PTFE.

Therefore it is particularly felt the need to find a PTFE dispersion in an organic solvent, to be utilized in particular as release agent from moulds, exhibiting the following characteristics:

(a) use of solvents having a low inflammability degree and low surface tension, not polluting, easily removable after the application on the substratum (solvents must not be retained to avoid formation of vapours during molding and then surface defects (bubbles) on moulded pieces);

(b) good stability to ageing and to external stresses (temperature variations, mechanical stirring, addition of electrolytes or other solvents, etc.);

(c) in case of separation of phases, easy PTFE redisperseability (for instance by simple stirring);

(d) high adhesion to the treated substratum, whereby no transfer on the moulded piece occurs and it is possible to carry out multiple moldings;

(e) high chemical inertia with respect to the components of the polymeric composition to be moulded, whereby no alteration either of the coating or of the surface of the molded pieces occurs.

(f) easiness of preparation and application;

(g) treatment reversibility, whereby it can be easily removed from the mould.

The Applicanmt has now surprisingly found that PTFE dispersions in an organic solvent meeting the requirements mentioned above can be obtained by employing as dispersing agent a product having a non fluorinated chain bound to a (per)fluoropolyoxyalkylenic chain, as defined hereinunder.

A first subject matter of the present invention is therefore a polytetrafluoroethylene (PTFE) dispersion in an organic solvent, comprising:

(a) from 2 to 40%, preferably from 15% to 30%, by weight of PTFE in powder form;

(b) from 50 to 95%, preferably from 65 to 80% by weight of an organic solvent; (c) from 0.5 to 10%, preferably from 1 to 5% by weight of a dispersing agent of formula:

$$(R_H-L)_y-(R_F-L)_xR_H \qquad (I)$$

wherein:

x is an integer from 1 to 3;

y is 0 or 1, with the proviso that x=1 when y=1;

$R_H$ is a x-functional radical having an alkylic or cycloalkylic $C_5$–$C_{10}$, or alkylarylic or arylalkylic $C_{10}$–$C_{50}$, linear or branched structure, optionally containing hydroxyl or $C_1$–$C_4$ alkoxy groups, or having a polyoxyalkylenic structure, wherein alkylene has from 2 to 4 carbon atoms and the number of oxyalkyl units is comprised between 5 and 70, preferably between 10 and 50;

$R_F$ is a (per)fluoropolyoxyalkylene radical having a number average molecular weight $M_n$ comprised between 350 and 2,000, preferably from 400 to 1,000;

L is a divalent organic group, bridging between $R_F$ and $R_H$, selected from:

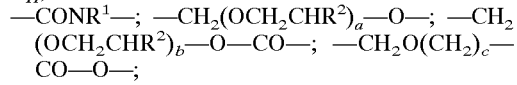

—$CONR^1$—; —$CH_2(OCH_2CHR^2)_a$—O—; —$CH_2(OCH_2CHR^2)_b$—O—CO—; —$CH_2O(CH_2)_c$—CO—O—;

wherein $R^1$ is —H or an alkyl $C_1$–$C_4$; $R^2$ is —H or a $C_1$–$C_2$ alkyl; a, b are integers from 0 to 6, prefrably from 0 to 2, c is a number from 1 to 3.

In case x=1, $R_H$ is a monovalent group, selected for instance from:

(i) —$(CH_2)_n E^1$, wherein: n is an integer from 5 to 50, preferably from 10 to 40; $E^1$ is —H;

(ii) —$(CH_2CH(CH_3)O)_p CH_2CHR^3 E^2$, wherein: p is an integer from 5 to 70, preferably from 10 to 50; $R^3$ is selectd from —H and —$CH_3$; $E^2$ is selected from —OH, $C_1$–$C_4$ alkoxy;

(iii) —$(CH_2CH_2O)_q$—$CH_2CH_2E_3$, wherein: q is an integer from 5 to 70, preferably from 10 to 25; $E^3$ is selected from —OH, $C_1$–$C_4$ alkoxy;

(iv) —$(CH_2CH_2O)_r (CH_2CH(CH_3)O)_s CH_2CHR^3 E^2$ wherein r+s is an integer from 5 to 70, prefrably from 10 to 50; the r/s ratio is comprised between 0.1 and 10, preferably between 0.5 and 5; $R^3$ is selected from —H and —$CH_3$; $R^4$ is selected from —OH, $C_1$–$C_4$ alkoxy.

In case x=2, $R_H$ is a divalent group, and can be selected from the groups indicated above whrein $E^1$, $E^2$, $E^3$, $E^4$ indicate covalent bonds.

In case x=3, $R_H$ is a trivalent group, for instance a group:

$CH_2$—$(OCH_2CHR^4)_t$—
$CH$—$(OCH_2CHR^4)_{t'}$—
$CH_2$—$(OCH_2CHR^4)_{t''}$— wherein $R^4$ is —H or an alkyl $C_1$–$C_2$, t is an integer from 3 to 10.

The (per)fluoropolyoxyalkylene group $R_F$ is formed by one or more repeating units, statistically distributed along the chain, selected for instance from:

—$(CF(CF_3)CF_2O)$—; —$(CF_2CF(CF_3)O)$—; —$(CF_2CF_2O)$—; —$(CFXO)$— wherein x is —F or —$CF_3$; —$(CYZ—CF_2CF_2O)$— wherein Y and Z, equal to or different from each other, are F, Cl or H.

When y=0, the $R_F$ group is monovalent and can be selected in particular from the following classes:

(a) T—O—$(CF_2CF(CF_3)O)_m(CFXO)_n$—CFX— 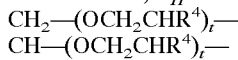  (II)

wherein:

T is a (per)fluoroalkyl group selected from:
—$CF_3$, —$C_2F_5$, —$C_3F_7$, —$CF_2Cl$, —$C_2F_4Cl$, —$C_3F_6Cl$; X is —F or —$CF_3$; m and n are numbers such that the n/m ratio is from 0.01 to 0.5 and the molecular weight is in the range indicated above;

(b) T'—O—$(CF_2CF_2O)_p(CF_2O)_q$—$CF_2$— (III)

wherein:

T' is a (per)fluoroalkyl group selected from:
—$CF_3$, —$C_2F_5$, —$CF_2Cl$, —$C_2F_4Cl$; p and q are numbers such that the ratio q/p is from 0.5 to 2 and the molecular weight is in the range indicated above;

(c) T''—O—$(CF_2CF(CF_3)O)_r$—$(CF_2CF_2O)_s$—$(CFX''O)_t$—CFX''— (IV)

wherein:

T'' is a (per)fluoroalkyl group selected from:
—$CF_3$, —$C_2F_5$, —$C_3F_7$, —$CF_2Cl$, —$C_2F_4Cl$, —$C_3F_6Cl$; X'' is —F or —$CF_3$; r, s and t are numbers such that r+s is comprised between 1 and 50, the ratio t/(r+s) is comprised between 0.01 and 0.05 and the molecular weight is in the range indicated above;

(d) T'''—O—$(CF(CF_3)CF_2O)_u$—$CF(CF_3)$— (V)

wherein:

T''' is —$C_2F_5$ or —$C_3F_7$; u is a number such that the molecular weight is in the range indicated above;

(e) T$^{IV}$—O—$(CYZ—CF_2CF_2O)_v$—CYZ—$CF_2$— (VI)

wherein:

Y and Z, equal or different from each other, are F, Cl or H; T$^{IV}$ is —$CF_3$, —$C_2F_5$ or —$C_3F_7$; v is a number such that the molecular weight is in the range indicated above;

(f) T$^V$—O—$(CF_2CF_2O)_w$—$CF_2$— (VII)

wherein:

T$^V$ is —$CF_3$ or —$C_2F_5$; w is a number such that the molecular weight is in the range indicated above.

When y=1, the $R_F$ group is divalent, and can be selected in particular from the following classes:

(a') —$CF_2$—O—$(CF_2CF_2O)_{p'}(CF_2O)_{q'}$—$CF_2$— (VIII)

wherein:

p' and q' are numbers such that the q'/p' ratio is comprised between 0.5 and 2 and the molecular weight is in the range indicated above;

(b') —CFX''—O—$(CF_2CF(CF_3)O)_{r'}$—$(CF_2CF_2O)_{s'}$—$(CFX''O)_{t'}$—CFX''— (IX)

wherein:

X'' is —F or —$CF_3$; r', s' and t' are numbers such that r'+s' is comprised between 1 and 50, the t'/(r'+s') ratio is between 0.01 and 0.05 and the molecular weight is in the range indicated above;

(c') —$CF(CF_3)(OCF_2CF(CF_3))_{u'}$—OR'$_f$O—$(CF(CF_3)CF_2O)_{u'}CF(CF_3)$— (X)

wherein:

R'$_f$ is a perfluoroalkylene $C_1$–$C_8$; u' is a number such that the molecular weight is in the range indicated above;

(d') —$CF_2CF_2O$—$(CF_2CF_2CF_2O)_{v'}$—$CF_2CF_2$— (XI)

wherein:

v' is a number such that the molecular weight is in the range indicated above:

(e') —$CF_2CH_2$—$(OCF_2CF_2CH_2O)_{w'}$—OR'$_f$O—$(CH_2CF_2CF_2O)_{w'}$—$CH_2CF_2$— (XII)

wherein:

R'$_f$ is a perfluoroalkylene $C_1$–$C_8$; w' is a number such that the molecular weight is in the range indicated above;

(f') —$CF_2$—O—$(CF_2CF_2O)_{x'}$—$CF_2$— (XIII)

wherein:

x' is a number such that the molecular weight is in the range indicated above;

A further subject matter of the present invention is the dispersing agents of formula (I), as defined above, and by the relevant preparation process.

The dispersing agents of the present invention have a high hydrolysis stability, whereby they can be easily sinthetized and stored for long time, and result sufficiently stable in both acid and basic environment.

Their preparation can be carried out starting from the corresponding mono- or di-functional (per) fluoropolyoxyalkylenes. In particular:

(1) when L is a —CO—NR$^1$— group, the corresponding (per)fluoropolyoxyalkylene functionalized with —CO—B groups, wherein B is —OR$^4$ (R$^4$=alkyl C$_1$–C$_4$) or —Cl or —F, can be reacted with a mono- or polyamine R$_H$(NHR$^1$)$_x$;

(2) when L is —CH$_2$(OCH$_2$CHR$^2$)$_a$—O—, the corresponding (per)fluoropolyoxyalkylene functionalized with alcoholate groups —CH$_2$(OCH$_2$CHR$^2$)$_a$O$^-$Me$^+$ (Me=alkaline metal) can be reacted with a compound R$_H$(X)$_x$ (X=—Cl, —Br, tosylate ion);

(3) when L is —CH$_2$(OCH$_2$CHR$^2$)$_b$—O—CO—, an esterification reaction can be carried out between the corresponding (per)fluoropolyoxyalkylene functionalized with groups —CH$_2$(OCH$_2$CHR$^2$)$_b$—OH and an acyl halide of formula R$_H$(COY)$_x$ (Y=—F, —Cl);

(4) when L is —CH$_2$O—(CH$_2$)$_c$—CO—O—, the corresponding (per)fluoropolyoxyalkylene functionalized with groups alcoholate —CH$_2$O$^-$Me$^+$ (Me=alkaline metal) can be reacted with an halogenated ketone of formula R$_H$(O—CO—(CH$_2$)$_c$—Z)$_x$ (Z=—Cl, —Br, tosylate ion).

Ther mono- or difunctional (per)fluoropolyoxyalkylenes are known products and can be prepared starting from the corresponding (per)fluoropolyoxyalkylenes having —COF end groups (see for instance GB-A-1,104,482, U.S. Pat. No. 3,715,378, U.S. Pat. No. 3,242,218, U.S. Pat. No. 4,647,413, EP-A-148,482, U.S. Pat. No. 4,523,039, EP-A-340,740, WO-A-90/03357, U.S. Pat. No. 3,810,874, EP-A-239,123, U.S. Pat. No. 5,149,842 and U.S. Pat. No. 5,258,110).

The PTFE in powder form consists of particles of sizes generally comprised between 1 and 15 μm, preferably between 2 and 5 μm. By PTFE it is meant both the homopolymer of tetrafluoroethylene and the copolymers of the latter with other fluorinated olefine monomers in amounts comprised between 0.1 and 10% by moles, such as hexafluoropropene, perfluoroalkylvinylethers, vinylidene fluoride, hexafluoroisobutene, chlorotrifluoroethylene, etc.

As organic solvents are preferably employed products having low surface tension, generally lower then 30 dyne/cm, and flash point higher than 10° C., preferably higher than 21° C. They can be selected for instance from the group consisting of:

(a) acyclic or cyclic, aliphatic or aromatic hydrocarbons having linear or branched chain, such as for instance, n- or iso-paraffins with at least 8 carbon atoms;

(b) aliphatic or cycloaliphatic alcohols, with linear or branched chain, having at least 5 carbon atoms, for instance n-octanol;

(c) aliphatic or cycloaliphatic ketones, with linear or branched chain, having at least 6 carbon atoms, for instance methylisobutylketone;

or their blends.

The preparation of the dispersions of the present invention can be carried out according to conventional techniques. A preferred preparation is the following. The dispersing agent in the molten state is added under stirring to the organic solvent previously heated to a temperature higher than the melting temperature of the dispersing agent, so as to obtain a limpid solution. The PTFE powder is gradually added to such solution, always by keeping the system under vigorous stirring. The resulting dispersion can be furtherly homogenized, for instance by blade ground plate or ball mill.

Other conventional components, such as oils or silicone resins, non-ionic surfactants of hydrocarbon type, etc., can be added to the dispersions of the present invention.

The dispersions of the present invention can generally be employed for the surface treatment of metals, glass fibers, and the like, in order to obtain a protective, lubricating and anti-adhesive coating. In particular, such dispersions are used as mould release agents in order to make the release easier of polymeric materials, both of thermoplastic and thermosetting type, such as polyvinylchloride, epoxy resins, polyurethanes, polyesters and the like.

Some working examples of the present invention are reported hereinunder, whose purpose is merely illustrative but not limitative of the scope of the invention itself.

EXAMPLE 1

Into a 2 l 3 neck flask 340 g of stearylamine were introduced. It was heated up to 70° C. so as to obtain the amine in the molten state. 950 g of an ester of formula:

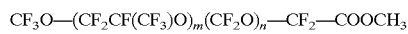

having m/n ratio equal to 30 and equivalent weight of 720, were then slowly dripped in the flask (for 30 min) and under stirring. By keeping the temperature at 70° C., the system was reacted for 4 hours until a limpid mixture was obtained. The IR analysis of the mixture has shown the presence of two absorptions at 1800 and 1710 cm$^{-1}$, attributable to the carbonyls of the ester and amide groups respectively. No basic reaction due to free amine was noticed. The methanol deriving from the reaction and the excess ester were then distilled under reduced pressure (final conditions: 0.8–1 mmHg, 110°–120° C.). The product thus obtained, having the formula:

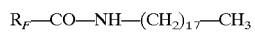

wherein R$_F$=CF$_3$O—(CF$_2$CF(CF$_3$)O)$_m$ (CF$_2$O)$_n$—CF$_2$—, appeared as a white wax, having melting point of 52° C. The IR analysis showed a band at 1710 cm$^{-1}$ relating to the amidic carbonyl, while the band at 1800 cm$^{-1}$ relating to the ester carbonyl was absent.

EXAMPLE 2

Into a 2 l 3 neck flask 830 g of an ester of formula:

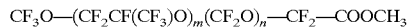

having m/n ratio equal to 30 and equivalent weight of 720, were mixed with 830 g of an amine liquid, at room temperature, of formula:

with equivalent weight equal to 575, commercialized by Texaco Chem. Co. as Jeffamina® M600. By keeping the temperature at 70° C., the system was reacted for 4 hours until a limpid mixture was obtained. The IR analysis of the mixture has shown the presence of two absorptions at 1800 and 1710 cm$^{-1}$, attributable to the carbonyls of the ester and amide groups respectively. No basic reaction due to free amine was noticed. The metahnol deriving from the reaction and the excess ester were then distilled under reduced pressure (final conditions: 0.8–1 mmHg, 110°–120° C.). The product thus obtained, having the formula:

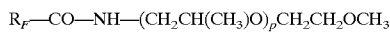

wherein $R_F=CF_3O-(CF_2CF(CF_3)O)_m(CF_2O)_n-CF_2-$, showed as a straw-coloured oil, having viscosity equal to 92 cSt and density of 1.5 (at 20° C.). The IR analysis showed a band at 1710 cm$^{-1}$ relating to the amidic carbonyl, while the band at 1800 cm$^{-1}$ relating to the ester carbonyl was absent.

EXAMPLE 3

200 g of an alcohol of formula:

having average molecular weight equal to 1040 and q/r ratio=1, obtained by reaction of isobutylic alcohol in alkaline medium with ethylene and propylene oxide, were treated with an excess (50 g) of chloroacetylchloride at 70°–80° C. until the evolvement of HCl ceased. The excess chloroacetylchloride was then distilled under reduced pressure (final conditions: 100 mmHg, 120° C.). An ester of formula

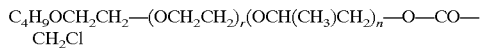

was thus obtained, which showed at IR analysis an absorption at 1740 cm$^{-1}$ attributable to the C=O ester group, and no absorbtion referable to residual —OH groups.

A solution was prepared in ter.butanol (500 ml) of an alcoholate corresponding to perfluoropolyoxyalkylene-diol of formula:

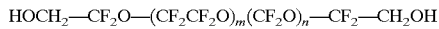

wherein the average molecular weight is 1600 and the m/n ratio=0.8, by stoichiometric addition of potassium terbutylate $(CH_3)_3C-O^-K^+$ at 155 g of said diol. The ester previously prepared was added to such solution. The mixture was reacted for 16 hours at 50° C., under strong stirring. At the end of the reaction, shown by the absence of free base, the mixture was filtered and the ter.butanol removed by distillation under reduced pressure (final conditions: 0.5 mmHg, 120° C.). At the IR analysis the thus obtained product did not show any longer the absorptions typical of the —OH groups, but only those due to the C=O ester. On the basis of the IR and $^{19}$F-NMR analysis, the following structure was determined:

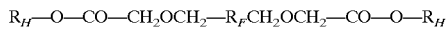

wherein:
$R_H=-(CH_2CH_2O)_r(CH_2CH(CH_3)O_sCH_2CH_2OC_4H_9$,
$R_F=-CF_2O-(CF_2CF_2O)_m(CF_2O)_n-CF_2-$.

The oil- and water-repellency properties of the dispersing agents of the present invention were evaluated by contact angle measurements of a drop of water and of a drop of hexadecane deposited on a steel plate treated with the product dissolved in isopropanol in amounts equal to 0.5 mg/cm$^2$ of product. The values reported in Table I are the average of the measurements carried out on 4 different points of the surface, on each of them 3 drops were deposited. As known, the higher the value of the contact angle is, the higher are the water- or oil-repellency properties of the treated surface.

Also the sliding properties were evaluated by friction coefficient measurements. A brass head of 0.5×2 cm area on which a load L (300 g) is applied, is let slide over a steel plate traeted with the product described above. The friction coefficient is given by the ratio (dimensionless) between friction force F (expressed as grams-force) and load L (in grams) (see the ASTM D 4518 standard). The results are reported in Table 1. For comparative purposes, Table 1 reports the values obtained further the application of the steel plate of the same amount of a perfluoropolyoxyalkylene (commercial product Fomblin® Y 25). In table 1 are reported also the measurements carried out by employing the PTFE dispersion of Example 6.

TABLE 1

| APPLIED | CONTACT ANGLE (°) | | FRICTION |
|---|---|---|---|
| PRODUCT | water | oil | COEFFICIENT |
| Ex. 1 | 100 | 80 | 0.17 |
| Ex. 2 | 60 | 30 | 0.27 |
| Ex. 6 | 110 | 100 | 0.07 |
| Fomblin$^{(R)}$ Y 25 | 95 | 60 | 0.18 |

EXAMPLE 4

The product prepared according to Example 1 was employed to prepare a PTFE dispersion in organic solvent as follows.

7.35 kg (9.32 l) of isoparaffine Isopar® J of Exxon were loaded in a 15 l cylindrical reactor, equipped with heating jacket, with turbine stirrer Rushton type, hopper and screw for loading powders. The solvent was brought to 60° C. and kept under stirring at 1000 rpm rate. 250 g of the dispersing agent of Example 1 in the molten state (melting point: 52° C.) were then added, thus obtaining a limpid solution. 2.40 kg of powder of PTFE Algoflon® L 203 (TFE copolymerized with about 3% by moles of hexafluoropropene) were then added gradually to the above solution in about 3 hours. The PTFE Algoflon® L 302 powder had particle average size lower than 5 μm and average molecular weight of about 300,000. When the PTFE addition was finished, the dispersion was kept under stirring at 50°–60° C. for about further 2 hours and then homogenized in a mixer Silverson type at room temperature for 10 min. A fluid homogeneous dispersion was thus obtained, containing 2.5% by weight of dispersing agent.

After cooling to room temperature, the stability of the formulation was evaluated according to the following method.

80 ml of PTFE dispersion were put in a 100 ml graduated cylinder; by maintaining the sample at rest, the amount (expressed as % by volume) of limpid solvent present on the surface after 4, 8, 24 and 48 hours was measured. The PTFE redisperseability was also measured on the sample after 48 hours storage. The test is positive if after manual stirring and subsequent transfer no PTFE residue is noticed on the bottom of the cylinder.

The results are reported in Table 2.

EXAMPLE 5 (COMPARATIVE)

A PTFE dispersion was prepared as described in Example 4, by using, instead of the fluorinated dispersing agent, a commercial non-ionic surfactant Tween® 80 (sorbitanmonooleate containing propylenoxidic units), in such amount as to obtain in the dispersion a concentration equal to 5% by weight. The results of the stability measurements, carried out as described above, are reported in Table 2.

EXAMPLE 6

A PTFE dispersion was prepared according to Example 4, by using as solvent 6.5 kg of mineral oil of turpentine type D30 of Exxon (paraffins mixture $C_9$–$C_{12}$), kept at 40° C., 500 g (5.0% by weight) of the dispersing agent prepared as described in Example 1 and 3.0 kg of PTFE Algoflon® L 203 powder. A fluid homogeneous dispersion, containing 5% by weight of dispersing agent was thus obtained.

After cooling to room temperature, the stability of the dispersion was measured as described above. The results are reported in Table 2.

The dispersion, diluted 1:4 with the same mineral oil of turpentine, was utilized for molding tests as follows.

The dispersion was applied by buffer on the internal surface of a steel mould heated at 50° C., so as to obtain an homogeneous and continuous film. After the solvent was dried for about 30 min, an epoxy resin Epikote® 828 was poured into the mould, containing Teta® as an acceleranting agent in weight ratio 100:8. The resin was crosslinked by heating at 100° C. for 2 hours. The mould was then open and the resin removed; it was examined the surface both of the molded piece, to check the possible presence of defects, and of the mould, to verify the possible presence of resin residues and/or the removal of the release agent. It was considered the number of possible consecutive mouldings without applying further release agent and without defects appearing on the moulded piece. It was possible to carry out 8 mouldings without noticing any drawback.

The same dispersion was moreover utilized for a moulding test equal to the previous one, by using, instead of the epoxy resin, a closed cell polyvinylchloride/foamed polyurethane mixture. The initial mould temperature was equal to 45° C. After the polymeric mixture was poured therein, the mould was heated for 12 min until the temperature of 180° C. was reached, and then it was kept at such a temperature for further 6 min. It was possible to carry out 4 moldings without applying again the dispersion. The mould was continuously used for 2 weeks without having to stop the cycle for cleaning. On the contrary, only one moulding was possible with a 30% silicone resin in chlorinated solvent utilized for the same test, after the first moulding it was necessary to apply again the release agent. The molding cycle was stopped after a week for the mould mechanical cleaning.

EXAMPLE 7 (COMPARATIVE)

Example 6 was repeated, without however adding any dispersing agent. The stability measurements of the dispersion are reported in Table 2. The dispersion, diluted 1:4, was utilized for moulding tests of epoxy resins as reported above. Already at the first moulding the molded piece appeared with a whitish surface, due to the deposit of PTFE powder, which it was necessary to remove by washing before proceeding to subsequent processings. It was not possible to carry out further mouldings without applying again the dispersion.

EXAMPLE 8

Example 6 was repeated by employing as dispersing agent the product prepared according to the above Example 2 in an amount equal to 8% by weight. The stability measurements of the dispersion are reported in Table 2.

EXAMPLE 9 (COMPARATIVE)

Example 6 was repeated by employing as dispersing agent a product of formula:

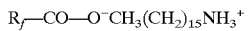

$R_f$=perfluoroalkyl) in amount equal to 2% by weight.

The dispersion was unstable, with formation of PTFE coagula and immediate separation of solvent.

TABLE 2

| | SEPARATED SOLVENT (% by volume) | | | | |
|---|---|---|---|---|---|
| Ex. | 4 hours | 8 hours | 4 hours | 48 hours | REDISPERSEABILITY |
| 4 | 0 | 0 | 0 | 0 | yes |
| 5(*) | 50 | 50 | 86 | 80 | no |
| 6 | 0 | 4 | 4 | 4 | yes |
| 7(*) | 50 | 50 | 80 | 80 | no |
| 8 | 4 | 10 | 50 | 50 | no |
| 9(*) | 80 | 80 | 80 | 80 | no |

(*)comparative

We claim:
1. A dispersion of polytetrafluoroethylene (PTFE) in an organic solvent, comprising:
   (A) from 2 to 40% by weight of PTFE in powder form;
   (B) from 50 to 95% by weight of an organic solvent;
   (C) from 0.5 to 10% by weight of a dispersing agent of formula:

wherein:
   x=1 and y=1;
   $R_H$ is a x-functional radical having an alkyl or cycloalkyl $C_5$–$C_{70}$ or alkylaryl or arylalkyl $C_{10}$–$C_{50}$, linear or branched structure, optionally containing hydroxyl or $C_1$–$C_4$ alkoxy groups, or having a polyoxyalkylenic structure, wherein alkylene has from 2 to 4 carbon atoms and the number of oxyalkylenic units is comprised between 5 and 70;
   $R_F$ is (per)fluoropolyoxyalkylene radical having a number average molecular weight $M_n$ comprised between 350 and 2,000;
   L is a divalent organic group, bridging between $R_F$ and $R_H$, selected from:
   —CONR$^1$—; —CH$_2$(OCH$_2$CHR$^2$)$_a$—O—; —CH$_2$(OCH$_2$CHR$^2$)$_b$—O—CO—; —CH$_2$O(CH$_2$)$_c$—CO—O—;
   wherein R$^1$ is —H or an $C_1$–$C_4$ alkyl; R$^2$ is —H or a $C_1$–$C_2$ alkyl; a, b, are integers from 0 to 6, c is a number from 1 to 3.

2. The dispersion according to claim 1, comprising:
   (a) from 15 to 30% by weight of PTFE in powder form;
   (b) from 65 to 80% by weight of an organic solvent;
   (c) from 1 to 5% by weight, of a dispersing agent of formula (I) of claim 1.

3. The dispersion according to claim 1 wherein $R_F$ has a number average molecular weight $M_n$ comprised between 400 and 1,000.

4. The dispersion according to claim 1, wherein in the formula (I) x=1, and $R_H$ is a monovalent group selected from:

(i) —$(CH_2)_nE^1$, wherein: n is an integer from 5 to 50; $E^1$ is —H;

(ii) —$(CH_2CH(CH_3)O)_pCH_2CHR^3E^2$, wherein: p is an integer from 5 to 70, $R^3$ is selected from —H and —$CH_3$; $E^2$ is selected from —OH, $C_1$–$C_4$ alkoxy;

(iii) —$(CH_2CH_2O)_q$—$CH_2CH_2E_3$, wherein: q is an integer from 5 to 70; $E^3$ is selected from —OH, $C_1$–$C_4$ alkoxy;

(iv) —$(CH_2CH_2O)_r(CH_2CH(CH_3)O)_sCH_2CHR^3E^2$ wherein r+s is an integer from 5 to 70; the r/s ratio is comprised between 0.1 and 10; $R^3$ is selected from —H and —$CH_3$; and $R^4$ is selected from —OH, $C_1$–$C_4$ alkoxy.

5. The dispersion according to claim 1, wherein the (per)fluoropolyoxyalkylene group $R_F$ is formed by one or more repeating units, statistically distributed along the chain, selected from:

—(CF ($CF_3$)$CF_2$O)—; —($CF_2$CF($CF_3$)O)—; —($CF_2CF_2$O)—; —(CFXO)— wherein X is —F or —$CF_3$; —(CYZ—$CF_2CF_2$O)— wherein Y and Z, equal to or different from each other, are F, Cl or H.

6. The dispersion according to claim 1, wherein PTFE is in powder form with particles sizes comprised between 1 and 15 μm.

7. The dispersion according to claim 1, wherein the organic solvent has surface tension lower than 30 dyne/cm and flash point higher than 10° C.

8. The dispersion according to claim 7, wherein the organic solvent is selected from the group consisting of:

(a) acyclic or cyclic, aliphatic or aromatic hydrocarbons having linear or branched chain;

(b) aliphatic or cycloaliphatic alcohols, with linear or branched chain, having at least 5 carbon atoms;

(c) aliphatic or cycloaliphatic ketones, with linear or branched chain, having at least 6 carbon atoms; and blends of a–c.

9. The dispersion according to claim 8, wherein the organic solvent is selected from n- or iso-paraffins with at least 8 carbon atoms, or their mixtures.

10. A method for treating the surfaces comprising applying to said surfaces the dispersion according to claim 1.

11. A method for improving the release properties of objects removed from molds comprising applying the dispersions of claim 1 to mold surfaces.

* * * * *